United States Patent [19]

Sugai et al.

[11] Patent Number: 5,468,874
[45] Date of Patent: Nov. 21, 1995

[54] BENZOTHIOPHENE/INDOLE-SUBSTITUTED MALEIMIDE DERIVATIVES, PHOTOCHROMIC MATERIAL COMPRISING SAID DERIVATIVES AND OPTICAL RECORDING MATERIAL USING THE SAME MATERIAL

[75] Inventors: Fumio Sugai; Masahiro Irie, both of Osaka, Japan

[73] Assignee: Mita Industrial Co., Ltd., Osaka, Japan

[21] Appl. No.: 218,258

[22] Filed: Mar. 25, 1994

[30] Foreign Application Priority Data

Mar. 26, 1993 [JP] Japan .................. 5-068926

[51] Int. Cl.$^6$ .................. C07D 495/12; C07D 409/14
[52] U.S. Cl. .................. 548/454; 548/417
[58] Field of Search .................. 548/454, 417

Primary Examiner—David B. Springer
Attorney, Agent, or Firm—Sherman and Shalloway

[57] ABSTRACT

A novel benzothiophene/indole-substituted maleimide derivative, a photochromic material and an optical recording material using the same. The benzothiophene/indole-substituted maleimide derivative is represented by the following formula (1):

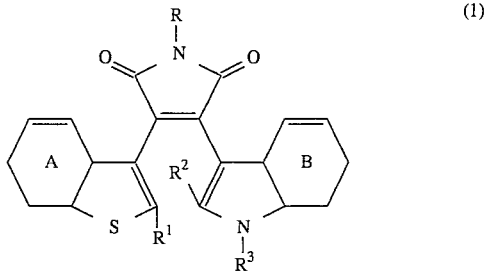

or the following formula (2):

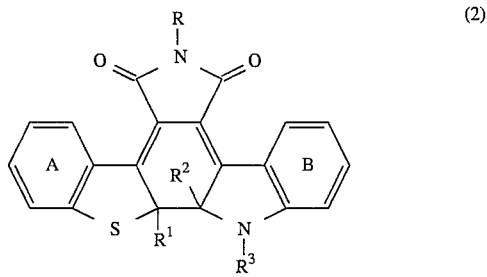

wherein R is a substituted or an unsubstituted monovalent hydrocarbon group, $R^1$ and $R^2$ are a hydrogen atom, an alkyl group, an alkylthio group or an alkoxy group under the condition where at least either one of them is an alkylthio group or an alkoxy group, $R^3$ is an alkyl group or an acyl group, and rings A and B may not be substituted or may be substituted with an alkyl group, an alkoxy group or a halogen atom, respectively.

9 Claims, 4 Drawing Sheets

5,468,874

BENZOTHIOPHENE/INDOLE-SUBSTITUTED MALEIMIDE DERIVATIVES, PHOTOCHROMIC MATERIAL COMPRISING SAID DERIVATIVES AND OPTICAL RECORDING MATERIAL USING THE SAME MATERIAL

BACKGROUND OF THE INVENTION

1. Field of the invention

The present invention relates to novel benzothiophene/indole-substituted maleimide derivatives, a photochromic material thereof and an optical recording material using said material.

2. Description of the Prior Art

Photochromic materials that develop color or extinguish color upon irradiation with light have heretofore been extensively used for a variety of applications such as optical filters like sunglasses, and as masking materials and display materials.

A variety of organic compounds have been known that serve as photochromic materials, such as spiropyran-type compounds (Japanese Patent Publication No. 28892/1970). According to Japanese Laid-Open Patent Publication No. 24245/1988 filed by the present inventors, furthermore, diheterocyclic-substituted ethene derivatives such as a 1,2-di(2,3,5-trimethylthienyl) maleic anhydride and the like have been proposed as photochromic materials.

The photochromic material develops color and extinguishes color due to the isomerization of a molecular structure accompanying the irradiation with light, and must satisfy such requirements as a high quantum yield for developing or extinguishing color, development of a vivid color, a large contrast between color developing and color extinction, and relatively stable thermal state for developing color or extinguishing color.

The present inventors have previously synthesized maleimide derivatives having a benzothiophene group and an indolyl group at the first position and the second position of a maleimide, i.e., synthesized the maleimide derivatives of the following formula

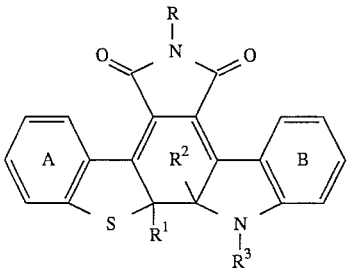

wherein R is a cyanomethyl group, $R^1$ and $R^2$ are methyl groups, respectively, and a hydrogen atom or a methoxy group is present at an ortho position with respect to a nitrogen atom in a ring B, and have discovered that the above derivatives are useful as photochromic materials.

These compounds are made compatible in a polymer (containing benzene), formed into a film (ring-opened product) to obtain a recording material, and are rendered to be a ring-closed product with visible light of 200 nm to 490 nm and are colored to write data therein. With this compound, however the isomerization factor from a ring-opened product into a ring-closed product (cyclohexadiene product) is still low, the contrast is low, and isomerized molecules are poorly maintained. Therefore, this compound is still not practical for use as an optical disk or an optical recording medium.

SUMMARY OF THE INVENTION

The present inventors have succeeded in synthesizing novel compounds that will be described below in detail and have discovered than these compounds are useful as photochromic materials.

That is, the object of the present invention is to provide novel maleimide derivatives having a benzothiophene group and an indolyl group at the first position and the second position, and further having an alkylthio group or an alkoxy group which is an electron-donating group at the second position of the benzothiophene group or the indolyl group that serves as an active site for forming a hexadiene ring.

Another object of the present invention is to provide a photochromic material which has a high quantum yield for developing or extinguishing color, develops a vivid color, exhibits a large contrast between color developing and color extinction, and exhibits a relatively stable state of color developing or color extinction at room temperature.

A further object of the present invention is to provide an optical disk or an optical recording material that features a high isomerization factor from a ring-opened product into a ring-closed product (cyclohexadiene product) upon irradiation with a laser beam, exhibits a high contrast and favorably maintains the isomerized molecules.

According to the present invention, there is provided a compound represented by the following formula (1):

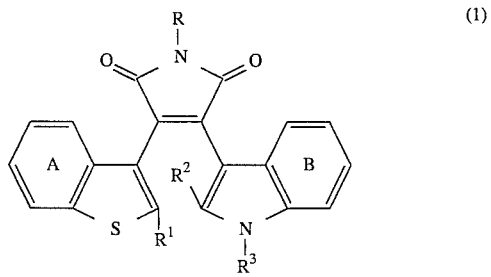

or the following formula (2):

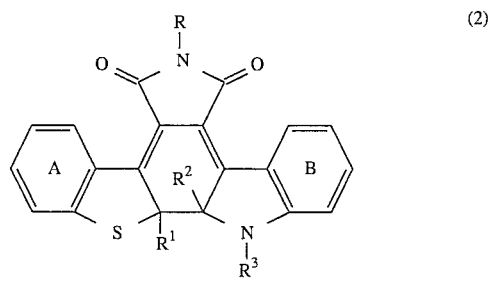

wherein R is a substituted or an unsubstituted monovalent hydrocarbon group, $R^1$ and $R^2$ are a hydrogen atom, an alkyl group, an alkylthio group or an alkoxy group under the condition where at least either one of them is an alkylthio group or an alkoxy group, $R^3$ is an alkyl group or an acyl group, and rings A and B may not be substituted or may be substituted with an alkyl group, an alkoxy group or a halogen atom, respectively.

According to the present invention, furthermore, there is provided a photochromic material comprising a compound represented by the above formula (1) or (2).

The present invention further provides an optical recording material containing a compound represented by the above formula (1) or (2).

The benzothiophene/indole-substituted maleimide derivatives of the present invention exhibit dense yellow color under the ring-opened state and exhibit vivid green color under the ring-closed state after being irradiated with a ray of active light. Furthermore, the derivatives have an alkylthio group or an alkoxy group at the second position of the thianaphthenyl group or the indolyl group. Therefore, the ring-closed product thereof exhibits a large quantum yield compared with compounds that have an alkyl group instead of the alkyl thio group.

The benzothiophene/indole-substituted maleimide derivatives of the present invention have an advantage in that the isomerization from a ring-opened product thereof of the formula (1) into a ring-closed product thereof of she formula (2) is highly efficiently carried out by a change in the polarity of the medium. That is, it has been known that the temperature of a polymer rises when it is irradiated with a laser beam and its polarity changes (becomes small). The present invention utilizes this feature in order to realize the optical recording maintaining a high contrast and improved efficiency.

The maleimide derivatives of the present invention exhibit a large quantum yield into the ring-closed product thereof, and can be used as photochromic materials for color filters and the like, and are particularly useful as optical recording materials.

DETAILED DESCRIPTION OF THE INVENTION

According to the present invention, the feature resides in such a chemical structure that the compound has, as substituents, a benzothiophene group and an indolyl group at the α-position and the β-position of a maleimide, and that the benzothiophene group or the indolyl group has, at the second position thereof, or, preferably, the benzothiophene group has, at the second position thereof, an alkylthio group or an alkoxy group that donates electron.

It was found that the maleimide derivatives of the present invention having a benzothiophene group and an indolyl group as substituents, exhibit excellent photochromic properties.

That is, in the present invention, the compounds of the formulas 1 and 2 are tautomers, and wherein the compound of the formula 1 is a ring-opened product and the compound of the formula 2 is a ring-closed product (cyclodiene ring). The compound of the formula 1 usually exhibits a dense yellow color and the compound of the formula 2 exhibits a bright and greenish transparent color.

The benzothiophene/indole-substituted maleimide derivative of the present invention turns into a ring-closed product of the formula 2 upon irradiation with a ray of visible light of 490 to 500 nm. The quantum yield of the ring-closed product varies depending upon the polarity of the medium in which the maleimide derivative exists, and increases with a decrease in the polarity.

The benzothiophene/indole-substituted maleimide derivative of the present invention has an alkylthio group or an alkoxy group at the second position of the benzothiophene group or the indolyl group and, hence, gives an advantage of gaining a larger quantum yield of a ring-closed product than a compound that has an alkyl group instead of the alkylthio group or the alkoxy group. As shown in Table 1 appearing later, when the quantum yield of a ring-closed product from the comparative compound in which $R^1$ and $R^2$ are both methyl groups in the formula 1 is regarded to be 1, then, the quantum yield of a ring-closed product from the compound of the present invention in which $R^1$ is a methylthio group and $R^2$ is a methyl group is 2.1. Thus, the maleimide derivative of the present invention makes it possible to accomplish an excellent quantum yield of the ring-closed product.

The benzothiophene/indole-substituted maleimide derivative of the present invention offers an advantage in that the ring-closed product of the formula 2 is isomerized into the ring-opened product of the formula 1 highly efficiently due to a change in the polarity of the medium. It has been known that the temperature of the polymer rises when it is irradiated with a laser beam, and the polarity of the polymer changes (decreases). The present invention utilizes this feature to efficiently accomplish the optical recording maintaining a high contrast.

Figure 1:
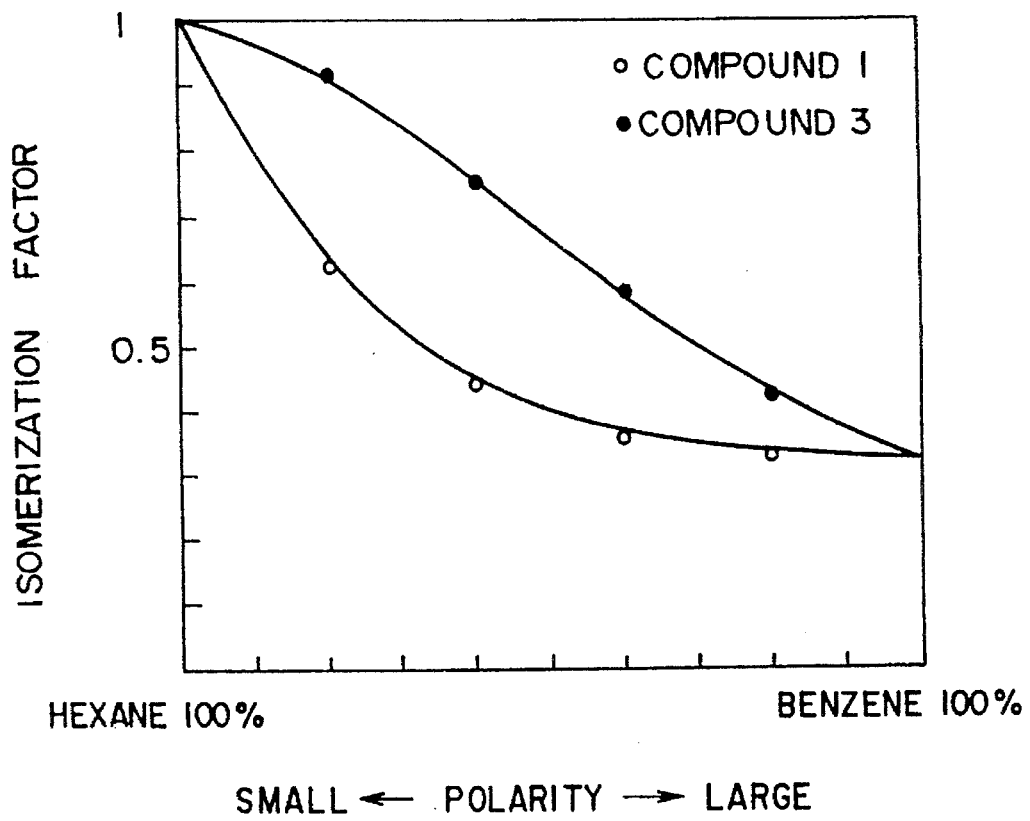
FIG. 1 is a graph plotting the isomerization factors (ratio of the amount of the ring-closed product with respect to the amount of the ring-closed product which is set to 1 in 100% of hexane) of a maleimide derivative of the present invention and a comparative maleimide derivative in media obtained by mixing a benzene having a large polarity and a hexane having a small polarity at various ratios.

FIG. 1 is a graph plotting the isomerization factors (ratio of the amount of the ring-closed product with respect to the amount of the ring-closed product which is set to 1 in 100% of hexane) of a maleimide derivative of the present invention (compound 3 mentioned later in which $R^1$ is a methylthio group and $R^2$ is a methyl group in equation 1) and a comparative maleimide derivative (compound 1 mentioned later in which $R^1$ and $R^2$ are both methyl groups in equation 2) in media obtained by mixing a benzene having a large polarity and a hexane having a small polarity at various ratios. In FIG. 1, the abscissa represents the polarity of the medium that is decreasing from the left toward the right manifesting an astonishing fact that the isomerization factor of the benzothiophene/indole-substituted maleimide derivative of the present invention from a ring-closed product thereof into a ring-opened product thereof changes greatly as the polarity decreases (details will be described later).

The maleimide derivative of the present invention gives a large quantum yield of the ring-closed product, and can be used as a photochromic material such as a color filter and the like and is, particularly, useful as an optical recording material.

Figure 2:
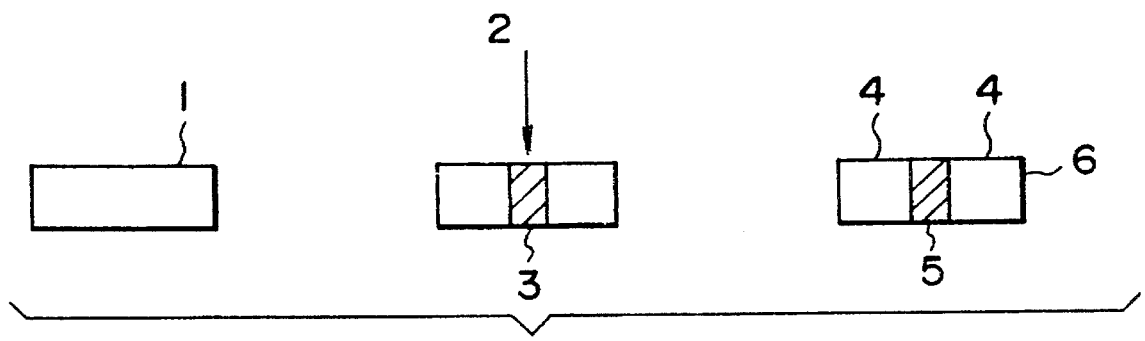
FIG. 2 is a diagram illustrating the operation of an optical recording material.

Referring to FIG. 2 illustrating the operation of the optical recording material, the optical recording material 1 comprises a polymer in which the benzothiophene/indole-substituted maleimide derivative of the present invention is dissolved, and is in a state of a ring-closed product thereof (indicated as a white area before writing data) being irradiated with a visible light of 490 to 500 nm. To write the data, the light 2 of 550 nm or longer is projected thereto. Being irradiated with the light of 550 nm or longer, the temperature rises at the irradiated portion 3, the polarity of the polymer decreases, the maleimide derivative is isomerized into a ring-opened product thereof in the irradiated portion 3 and develops a color. As the writing finishes, there is formed a positive recorded material 6 consisting of a highly transparent background 4 and a colored image portion 5. The optical recording material 1 is heated to render it entirely transparent, and is irradiated with light of 550 nm or longer to develop a color, so that it is entirely rendered opaque.

[Maleimide Derivatives]

in the maleimide derivatives of the formulas 1 and 2 of the present invention, R is a substituted or an unsubstituted monovalent hydrocarbon group which may be an alkyl group such as a methyl group an ethyl group, a propyl group or a butyl group, an aryl group such as a phenyl group or a tolyl group, or an aralkyl group such as a benzyl group or a phenethyl group. A particularly preferred example is a lower alkyl group with not more than 4 carbon atoms.

The monovalent hydrocarbon group may or may not be substituted. Preferred examples of the substituted group include a cyano group, an amide group, a carboxyl group and an alkoxycarbonyl group. Among them, the cyano group is preferred.

Each of $R^1$ and $R^2$ at the second position of the benzothiophene group and the indolyl group can be a hydrogen atom, an alkyl group or an alkylthio group under the condition where at least either one of them is the alkyl group or the alkylthio group. Preferred examples of the alkyl group are lower alkyl groups having not more than 4 carbon atoms such as a methyl group, an ethyl group, a propyl group and a butyl group. Among them, the methyl group is particularly preferred having less steric hindrance. Preferred examples of the alkyl thio group or the alkoxy group are groups represented by $-XR_4$ (wherein $R^4$ is an alkyl group, and X is an oxygen atom or a sulfur atom), and particularly lower alkoxy groups having not more than 4 carbon atoms such as a methylthio group, an ethylthio group, a methoxy group an ethoxy group, a propoxy group and a butoxy group. It is desired that the alkyl thio group or the alkoxy group is bonded to the second position of the thianaphthenyl group, and that the alkyl group is bonded to the second position of the indolyl group.

An alkyl group or an acyl group is introduced to the nitrogen atom of the indolyl group for the purpose of protection. Examples of the alkyl group are those having up to 26 carbon atoms. From the standpoint of compatibility to the polymer, however, it is desired to use an alkyl group having 8 or more carbon atoms, such as an ethylhexyl group, a lauryl group, a palmityl group or a stearyl group. Examples of the acyl group include an acetyl group, a propionyl group, a lauroyl group, a palmitoyl group, and a stearoyl group.

The benzene ring A of the benzothiophene group and the benzene ring B of the indolyl group may not be substituted or may be substituted with an alkyl group, an alkoxy group or a halogen atom. The alkyl group should be a lower alkyl group mentioned already and the alkoxy group should be a lower alkoxy group such as a methoxy group, an ethoxy group, a propoxy group or a butoxy group.

[Method of Synthesis]

A maleimide derivative of the present invention is synthesized by condensing and, at the same time, dehydrating and cyclizing an indolyl-3-oxalylamide derivative represented by the following formula (3)

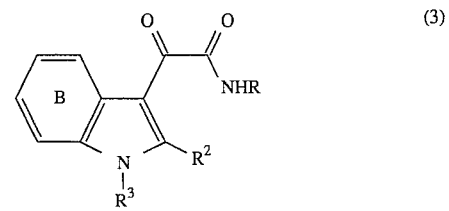

and a thianaphthenyl-3-acetyl halide derivative represented by the following formula (4)

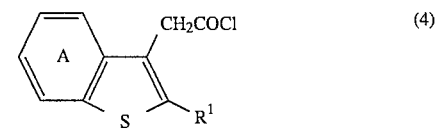

The condensation reaction removes the hydrochloric acid, and is carried out in the presence of an acid binder such as amines. The dehydration and cyclization into a maleimide ring are carried out in the presence of a dehydrating/condensing agent such as an anhydrous magnesium sulfate. In the above formulas (3) and (4), the groups $R^1$ to $R^3$ are the same as those of the formulas (1) and (2).

The indolyl-3-oxalylamide derivative of the formula (3) and, particularly, the one in which $R^2$ is a hydrogen atom is synthesized in a manner as described below.

That is, the alkyl group or the acyl group is introduced to the position of a nitrogen atom of indoles represented by the following formula (3a)

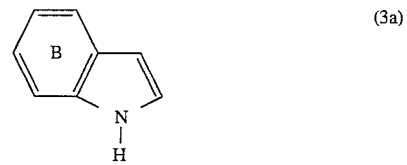

to obtain an N-alkyl or an acyl derivative of the following formula (3b)

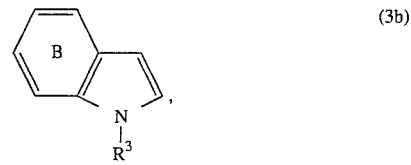

The alkyl group or the acyl group is introduced by using an alkyl halide or an acyl halide and an acid binder in combination.

The indole derivative of the formula (3b), the corresponding amines and oxalyl halide are reacted in the presence of the acid binder to form an indolyl-3-oxalylamide derivative group of the formula (3). When R is a hydrocarbon group having a cyano group, there should be used, as the abovementioned amines, ω-aminonitrile derivatives and, particularly, acid addition salts thereof. When the nitrile is hydrolyzed partly or entirely, there is obtained an amide derivative or a carboxyl derivative which is then esterified by a widely known method to obtain an ester derivative thereof. Therefore, if they are reacted with the derivatives of the formula (3b), there are obtained compounds of the formula (3) wherein R is a hydrocarbon group with various substitutents.

There has been known a compound in which an alkoxy group is introduced to the second position of the indole of the formula (3a). Therefore, the compound of the formula (3) in which $R^2$ alkoxy group can be prepared by reacting the above compound of the formula (3a) as a starting material.

Furthermore, the compound of the formula (3) in which $R^2$ is a thioalkyl group is synthesized by reacting an alkyl disulfate and an alkyl lithium upon the indoles of the formula (3a), and by reacting these indoles as starting substances.

When $R^2$ is an alkyl group, an alkyl iodine and an alkyl lithium are acted upon the indoles of the formula (3a) to introduce an alkyl group to the second position. These indoles are then reacted as starting substances.

Furthermore, a benzothiophene-3-acetyl halide derivative of the formula (4) in which R1 is a hydrogen atom is synthesized through the following passage.

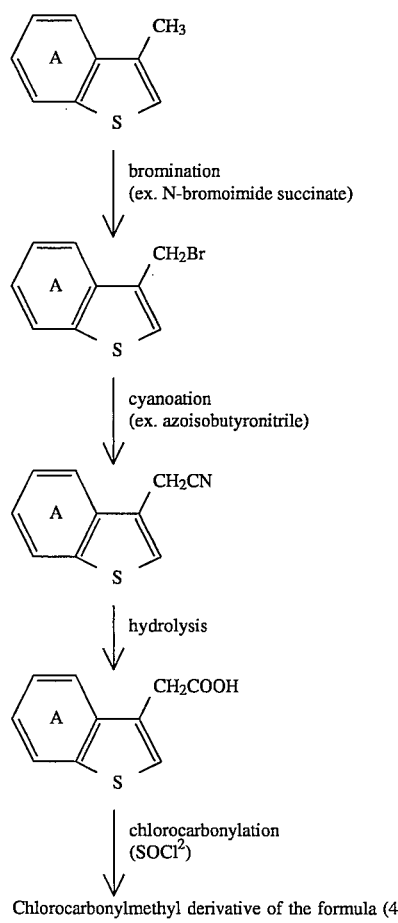

Chlorocarbonylmethyl derivative of the formula (4)

A compound of the formula (4a) in which an alkoxy group is introduced to the second position has been known. Therefore, the derivative of the formula (4) in which $R^1$ is an alkoxy group is prepared by reacting the above compound as a starting material.

The derivative of the formula (4) in which $R^1$ is a naphthyl group is synthesized by acting an alkyl disulfate and an alkyl lithium upon the 3-methylbenzothiophene of the formula (4a) to introduce a thioalkyl group to the second position thereof, and reacting this compound as a starting material.

The derivative of the formula (4) in which $R^1$ is an alkyl group is synthesized by using an alkyl iodine instead of the alkyl disulfate to introduce an alkyl group to the second position of the compound of the formula (4a), and reacting this compound as a starting material.

[Applications]

The maleimide derivatives of the present invention are useful as photochromic materials. That is, the maleimide derivatives are dissolved in a polymer which is then formed into a film or into any article so as to be used as photochromic materials.

The maleimide derivatives are dissolved in the polymer as described below. That is, a solution of maleimide derivatives is dissolved in a solution of the polymer that has been prepared in advance, and the resulting solution is formed into a film or is molded into an article by such means as casting or the like. According to another method, maleimide derivatives are dissolved in a thermosetting monomer or prepolymer which is then formed into a film or is molded into an article by such a means as casting or the like followed by curing by polymerization.

As the polymer, there is used a resin having excellent optical properties, such as a styrene type polymer an acrylic type polymer, a styrene acrylic type copolymer or a carbonate type polymer.

Examples of the monomer of the type which cures upon polymerization include an ethyl acrylate a methyl methacrylate, a 2-ethylhexyl acrylate, a mono- or di-ethyl maleate, a vinyl acetate, a vinyl propionate, an acrylamide, a methacrylamide, a maleimide, an acrolein, a methacrolein, a vinylmethyl ketone, a vinylbutyl ketone, an acrylonitriie, a methacrylonitrile, a γ-hydroxypropyl methacrylate, a β-hydroxyethyl acrylate, a vinylmethyl ether, a vinylethyl ether, an allyl ethyl ether, a glycidyl acrylate, a glycidyl methacrylate, a glycidylvinyl ether, a styrene, as well as polyfunctional monomers such as a polyalkylenepolyol(meth)acrylic acid ester, a bisdiethyleneglycol carbonate and a divinyl benzene, which can be used in combination with a radical initiator.

During the polymerization, no trouble is caused by the reaction such as of grafting between the benzothiophene/indole-substituted maleimide derivatives of she present invention and the polymer.

The maleimide derivative of the present invention can be used by itself as a photochromic material and can further be used as a photochromic material in combination with other photochromic materials. In the latter case, the color tone that develops can be adjusted to any desired color tone.

The polymer in which the maleimide derivatives are dissolved can be used alone as an optical recording material. Usually, however, a polymer composition in which the maleimide derivatives are dissolved is applied onto the surface of a plastic film such as of a biaxially stretched PET to form a recording layer. For those applications where the ray of light needs not pass through, a paper or a metal foil can be used as a substrate.

A ray of visible light of 490 nm or 550 nm is advantageously used as a source of light for extinguishing the color of the maleimide derivative of the present invention. As a laser beam which serves as a source of heat for writing, on the other hand, there is used a semiconductor laser such as of helium, neon or argon ions emitting light of 550 nm or longer, or a solid laser such as of ruby or a glass.

EXAMPLES

[Synthesis Example 1 (Comparative Compound)]

(1) Synthesis of a 2-methylbenzothiophene

A THF (tetrahydrofurane) solution containing 2.0 g (0.015 mmol) of a benzophene was cooled to −30° C., and to which was dropwisely added 14 ml of a hexane solution containing n-BuLi, and the mixture was stirred at −30° C. to −10° C. for two hours. The mixture was cooled again to −50° C. followed by the dropwise addition of THF containing 3.2 g (0.023 mol) of MeI, and the mixture was stirred overnight.

The water was added and the product was extracted with ether three times and dried using an anhydrous magnesium sulfate. Then, after the solvent was distilled off, the product was refined by a column chromatography using hexane as a developer thereby to obtain 2.1 g of a 2-methylbenzothiophene, yield 94.6%.

(2) Synthesis of a 2-methyl-3-chloromethylbenzothiophene

To 10 ml of a dichloromethane containing 1.5 g (10.0 mmol) of a 2-methylbenzothiophene was dropwisely added 5 ml (68 mmol) of a chloromethyl methyl ether at room temperature, and to which was then added 0.1 g (0.70 mmol) of zinc chloride. The mixture was stirred at room temperature for one hour. The water was added thereto, and the product was extracted with chloroform and was dried using the anhydrous magnesium sulfate. The solvent was distilled off to obtain an object compound.

(3) Synthesis of a 2-methyl-3-cyanomethylbenzothiophene

To the above 2-methyl-3-chloromethylbenzothiophene were added 10 ml of water, 1.5 g of NaCN and 0.2 g of a tetra-n-butylammonium bromide. The mixture was refluxed for four hours. After cooled, 10 ml of a 5% NaOH was added thereto, the product was extracted with chloroform and was dried using the anhydrous magnesium sulfate. The solvent was distilled off, and the product was refined by the column chromatography using hexane and ester of acetoacetic acid as a developer to obtain 0.883 g of an object compound, yield 47.0%.

(4) Synthesis of a 2-methyl-3-carboxymethylbenzothiophene 0.6 Grams (3.2 mmol) of a 2-methyl-3-cyanomethylbenzothiophene and 15 ml of a 20% KOH were refluxed for three hours. After left to cool, 1N HCl was added thereto, and the precipitated crystals were filtered and dried to obtain 0.54 g of an object compound, yield 82.0%.

(5) Synthesis of a 2-methyl-N-octadecylindole

35 Milliliters of a DMSO (dimethylsulfoxide) was cooled with ice, 2.0 g (50 mmol) of 60% NaH washed with hexane was added thereto, followed by the dropwise addition of 15 ml of the DMSO containing 63.3 g (25 mmol) of a 2-methylindole at room temperature. After the dropwise addition, the mixture was stirred at 35° C. for one hour, cooled again with ice, and to which was dropwisely added 0.83 g (25 mmol) of an octadecyl bromide. The mixture was stirred at room temperature for one hour, poured into the water, extracted with benzene and dried using the anhydrous magnesium sulfate. After the solvent was distilled off, the product was refined by the silica gel chromatography (hexane:chloroform=3:1) to obtain 8.62 g of an object compound, yield 90.0%.

(6) Synthesis of a 2-methyl-N-octadecylindolyl-3-oxalyl-N-cyanomethylamide

A mixture solution of 492 mg (2.34 mmol) of an aminoacetonitrile sulfate, 0.86 ml (0.24 mmol) of a triethylamine and 10 ml of a dichloromethane was refluxed for six hours and was then left to cool.

Moreover, 0.6 g (1.56 mmol) of the 2-methyl-N-octadecylindole synthesized above and 5 ml of the dichloromethane were cooled with ice in a separate container, followed by the dropwise addition of 0.2 g (1.5 mmol) of an oxalyl chloride. The mixture was stirred for one hour. This reaction solution was dropwisely added at room temperature to the reaction solution obtained above. The mixture was stirred overnight and the water was added thereto. The product was extracted with chloroform, dried by using the anhydrous magnesium sulfate, and the solvent was distilled off. The obtained solid material was recrystallized with hexane, filtered and was dried to obtain 0.62 g of an object substance, yield 80.0%.

(7) Synthesis of an α-(2-methylthianaphthenyl-3-)-β-(2-methyl-N-octadecylindolyl-3-)-N-cyanomethylmaleimide [Compound 1]

To 0.1 g ($4.9 \times 10^{-4}$ mol) of a 2-methyl-3-carboxymethylbenzothiophene was dropwisely added 6 ml of a thionyl chloride at room temperature, and the mixture was stirred for one hour. After the unreacted thionyl chloride was distilled off, 10 ml of a dichloromethane was further added thereto.

Then, in a separate container was prepared a mixture solution of 0.12 g ($2.5 \times 10^{-4}$ mol) of a 2-methyl-N-octadecylindolyl- 3-oxalyl-N-cyanomethylamide, 5 ml of a triethylamine and 10 ml of a dichloromethane. To this mixture solution was dropwisely added a solution of the dichloromethane prepared above, and the mixture was stirred overnight. Then, the product was extracted with a chloroform, washed with water, washed with hydrochloric acid, dried using the anhydrous magnesium sulfate, and the solvent was distilled off. The product was then refined by the silica gel column chromatography (using a developer of hexane:ethyl acetate=2:1), and was separated using a plate to obtain 0.10 g of an object product yield 64.0%

[Synthesis Example 2 (Comparative Compound)]

A 2-methyl-5-methoxy-N-octadecylindolyl-3-oxalyl-N-cyanomethylamide was synthesized in the same manner as the above Synthesis Example 1 but using a 2-methyl-5-methoxyindole instead of the 2-methylindole used in the synthesis method (5). Then, by using this compound, an α -(2-methylthianaphthenyl-3-)-β-(2-methyl-5-methoxy-N-octadecylindolyl- 3-)-N-cyanomethylmaleimide [compound 2] was synthesized in the same manner as in the Synthesis Example 1.

[Synthesis Example 3 (Compound of the Invention)]

(8) Synthesis of a 2-methylthio-3-methylbenzothiophene

12 Milliliters of the THF containing 1.5 g (10 mmol) of a 3-methylbenzothiophene was cooled to −30° C., and to which was dropwisely added 7.5 ml (12 mmol) of hexane containing n-BuLi, and the mixture was stirred at −30° C. to −10° C. for two hours. Then, 1.1 g (12 mmol) of MeS2 was dropwisely added thereto at −60° C. After stirred overnight, there were added the water and an aqueous solution of sodium hypochlorite, and the mixture was stirred and MeH was removed. The mixture was cooled with ice, a concentrated HCl was added thereto to make the mixture acidic. The product was extracted with ether, washed with water, dried using the anhydrous magnesium sulfate, and the solvent was distilled off. The product was refined by the silica gel column chromatography (using hexane as a developer) to obtain 1.9 g of a desired object, yield 97.9%.

(9) Synthesis of a 2-methylthio-3-cyanomethylbenzothiophene

To 10 ml of benzene containing 0.5 g (2.6 mmol) of a 2-methylthio-3-methyl-benzothiophene were added 0.46 g (2.6 mmol) of an NBS (N-bromoimide succinate) and 0.21 g (1.3 mmol) of an AIBN (azoisobutylonitrile), and the mixture was stirred at 60° C. for three hours. The water was poured, the product was extracted with chloroform and was dried using the anhydrous magnesium sulfate, and the solvent was distilled off. The product was added to a mixture solution of 10 ml of water, 0.2 g (4.0 mmol) of an NaCN and 0.13 g (4.0 mmol) of a tetra-n-butylammonium bromide, and the mixture was refluxed for five hours. The mixture was poured into the water, extracted with chloroform, dried, and was refined by the silica gel column chromatography (developer, hexane:ethyl acetate= 3:1) to obtain 0.30 g of an object product, yield 52.7%.

(10) Synthesis of a 2-methylthio-3-carboxymethylbenzothiophene

An aqueous solution of 20% of KOH containing 0.23 g (1.1 mmol) of a 2-methylthio-3-cyanomethyl-benzothiophene was refluxed for three hours. After left to cool, the water was added thereto and 1N HCl was added thereto while cooling the mixture with ice. The precipitated crystals were filtered and dried to obtain 0.189 g of an object product, yield 72.2%.

(11) Synthesis of an α-(2-methylthio-thianaphthenyl-3-)-β-(2-methyl-N-octadecylindolyl-3-)-N-cyanomethyl maleimide [Compound 3]

10 Milliliters of a thionyl chloride was added to 0.15 g (0.63 mmol) of a 2-methylthio-3-carboxymethylbenzothiophene, and the mixture was stirred at room temperature for one hour.

Then, the unreacted thionyl chloride was distilled off and 10 ml of a dichloromethane was added thereto.

0.20 Grams (0.38 mmol) of a 2-methyl-N-octadecylindolyl-3-oxalyl-N-cyanomethylamide, 10 ml of a dichloromethane and 5 ml of a triethylamine were introduced into a separate container, and were stirred. The mixture solution was then dropwisely added to the dichloromethane solution prepared above, and the mixture was stirred overnight at room temperature.

The product was then extracted with chloroform, washed with water, washed with hydrochloric acid, dried by using the anhydrous magnesium sulfate, and the solvent was distilled off. The product was then refined by the silica gel column chromatography (developer, hexane:ethyl acetate= 2:1), and was separated by using a plate to obtain 0.127 g of an object product yield 29.0%.

[Synthesis Example 4 (Compound of the Invention)]

Figure 3:
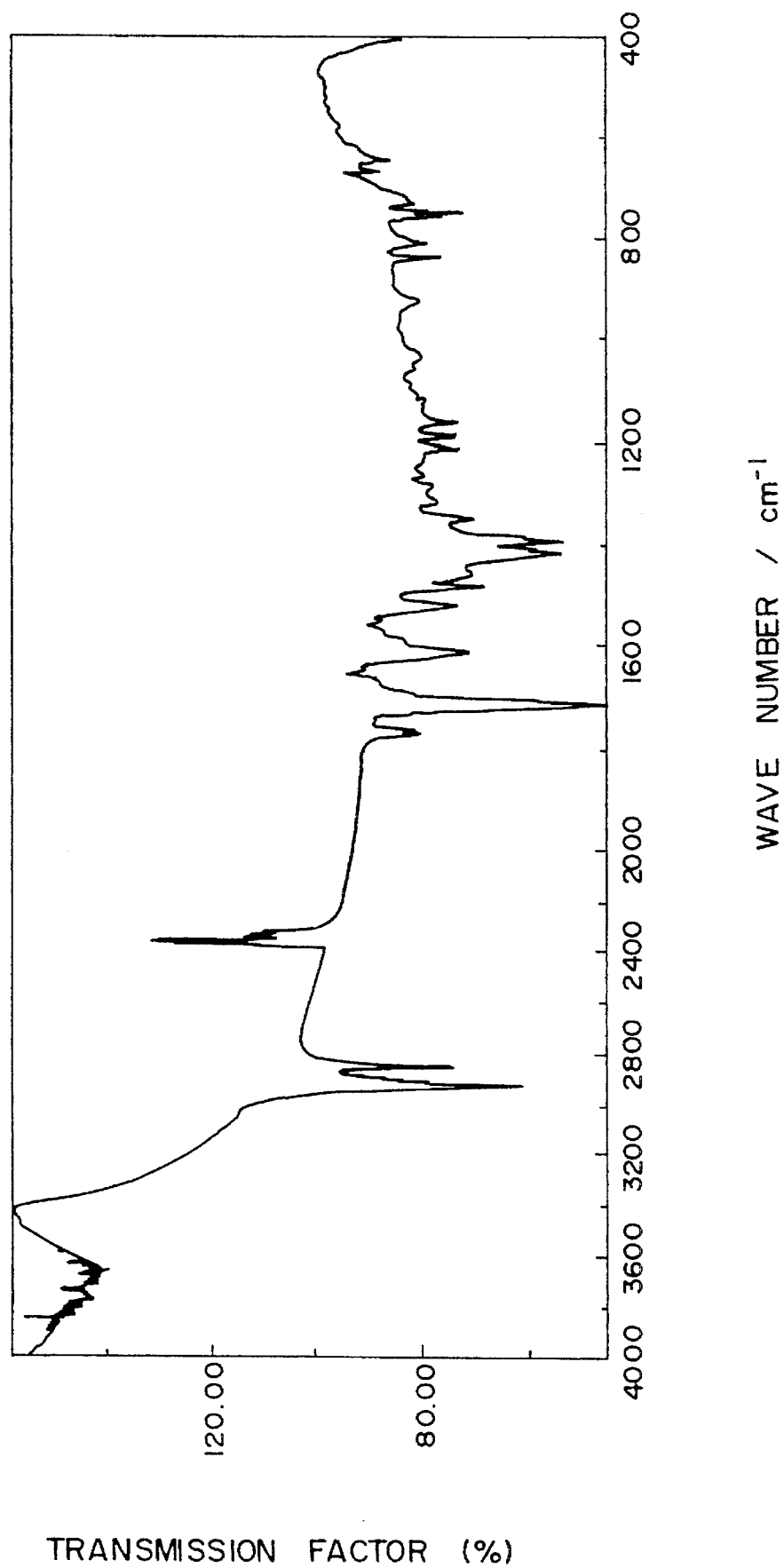
FIG. 3 is a diagram of an infrared-ray spectrum of a compound 4 of an Example.

A 2-methyl-5-methoxy-N-octadecylindolyl-3-oxalyl-N-cyanomethylamide was synthesized in the same manner as in the Synthesis Example 1 but using a 2-methyl-5-methoxyindole instead of the 2-methylindole used in the synthesis method (5). By using the above compound, an α-(2-methylthio-thianaphthenyl-3-)-β-(2-methyl-5-methoxy-N-octadecylindolyl-3-)-N-cyanomethylmaleimide [compound 4] was synthesized in the same manner as in the Synthesis Example 3. The results of analysis were as follows:

| Elemental analysis: | C | H | N |
| --- | --- | --- | --- |
| Calculated (%) | 71.13 | 7.63 | 5.78 |
| Measured (%) | 71.22 | 7.80 | 5.98 |
| Melting Point: | | 78.0° C. | |
| Infrared-ray spectrum: | | shown in FIG. 3 | |

[Synthesis Example 5 (Compound of the Invention)]

A 2-ethylthio-3-methylbenzothiophene was synthesized in the same manner as the synthesis method (8) of the Synthesis Example 3 but using an ethyl sulfate in the same molar amount instead of the methyl disulfate used in the synthesis method (8) and, from this compound was synthesized an α-(2-ethylthio-thianaphthenyl-3-)-β-(2-methyl-N-octadecylindolyl-3-)-N-cyanomethylmaleimide [compound 5] in the same manner as in the Synthesis Example 3.

[Synthesis Example 6 (Compound of the Invention)]

A 2-methyl-5-methoxy-N-octadecylindolyl-3-oxalyl-N-cyanomethylamide was synthesized in the same manner as in the Synthesis Example 1 but using a 2-methyl-5-methoxyindole instead of the 2-methylindole used in the synthesis method (5) of the Synthesis Example 4. Then, using the above compound, an α-(2-ethylthio-thianaphthenyl- 3-)-β-(2-methyl-5-methoxy-N-octadecylindolyl- 3-)-N-cyanomethylmaleimide [compound 6] was synthesized in the same manner as in the Synthesis Example 3.

Figure 4:
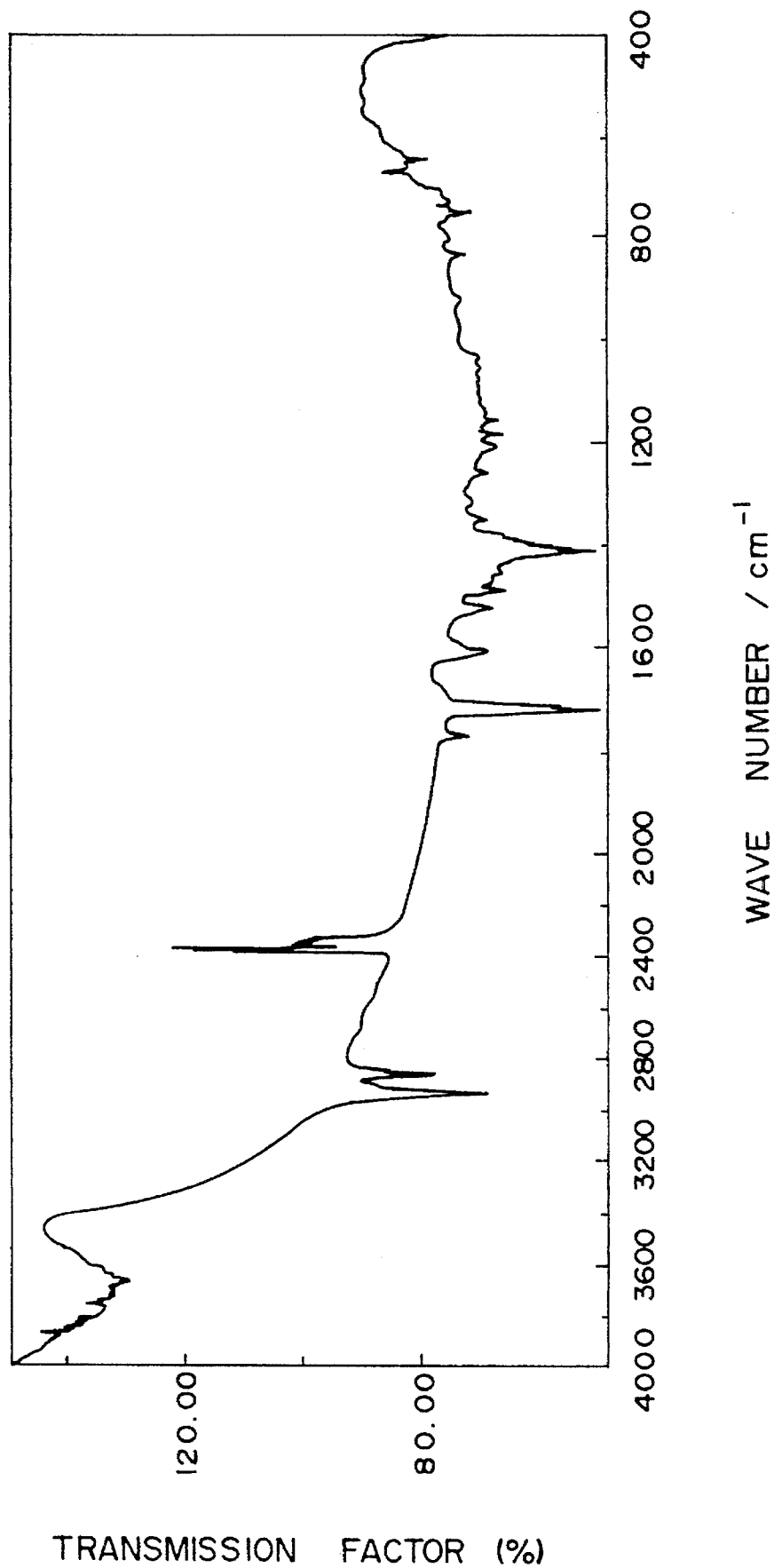
FIG. 4 is a diagram of an infrared-ray spectrum of a compound 6 of an Example.

The results of analysis were as follows:

| Elemental analysis: | C | H | N |
| --- | --- | --- | --- |
| Calculated (%): | 71.4 | 7.76 | 5.67 |
| Measured (%): | 71.52 | 7.83 | 5.72 |
| Melting point: | | 89.2° C. | |
| Infrared-ray spectrum: | | shown in FIG. 4 | |

[Synthesis Example 7 (Compound of the Invention)]

0.158 Grams (0.712 mmol) of a 2-methoxy-3benzothienylacetic acid and 14 ml of dry benzene were introduced into 50 ml of a three neck distillation flask, followed by the addition of 0.14 ml (1.78 mmol) of an oxalyl chloride at room temperature. The mixture was stirred at room temperature for about four hours and was then heated and refluxed for 20 minutes. The solvent and the oxalyl chloride were distilled off, and the product was dissolved in 5 ml of a 1,2-dichloroethane which was then dropwisely added at room temperature to a mixture solution of 0.375 g (0.71 mmol) of an N-octadecyl-2-methyl- 3-(N-cyanomethyloxamoyl) indole, 5 ml of a triethylamine and 15 ml of a dichloromethane that had been prepared in advance. After stirred for about 40 hours at room temperature, the water was added thereto and the product was extracted with chloroform. The organic layer was washed with dilute hydrochloric acid, washed with water, and was then dried using the anhydrous magnesium sulfate. The solvent was distilled off, and the obtained solid substance was separated using the silica gel column no obtain 0.342 g of a red and solid 2-(2-methoxy-3-benzothienyl)-3-(N-octadecyl-2-methyl-5-methoxy-3 -indolyl)-N-cyanomethylmaleimide [compound 7], yield 67.8%.

The results of analysis were as follows:

| Elemental analysis: | H | C | N |
| --- | --- | --- | --- |
| Calculated (%): | 7.81 | 72.74 | 5.92 |
| Measured (%) | 7.84 | 72.87 | 5.85 |
| Melting point: | | 89.6° C. | |

[Example 1]

The compounds 1, 2, 3, 4, 5 and 6 were dissolved in toluene, and a polystyrene was dissolved in this solution in such amounts that the concentrations of these compounds in the polystyrene were 0.2 mol % per a styrene unit. The solution was then applied onto a slide glass such that the thickness of the film after being dried was 100 μm thereby to obtain a laminated plate.

The photochromic layers all exhibited a vivid green color before they were irradiated with the light of 550 nm or longer, and exhibited a dense yellow color after they were irradiated with the light of 550 nm or longer.

[Example 2]

A solution of a solvent of hexane in which the compound 4 is dissolved ($1 \times 10^{-1}$ mol/l) was irradiated with an excitation wavelength to close the ring to a sufficient degree. By using a liquid chromatography, the solution was separated into a ring-opened product thereof and a ring-closed product thereof.

Figure 5:
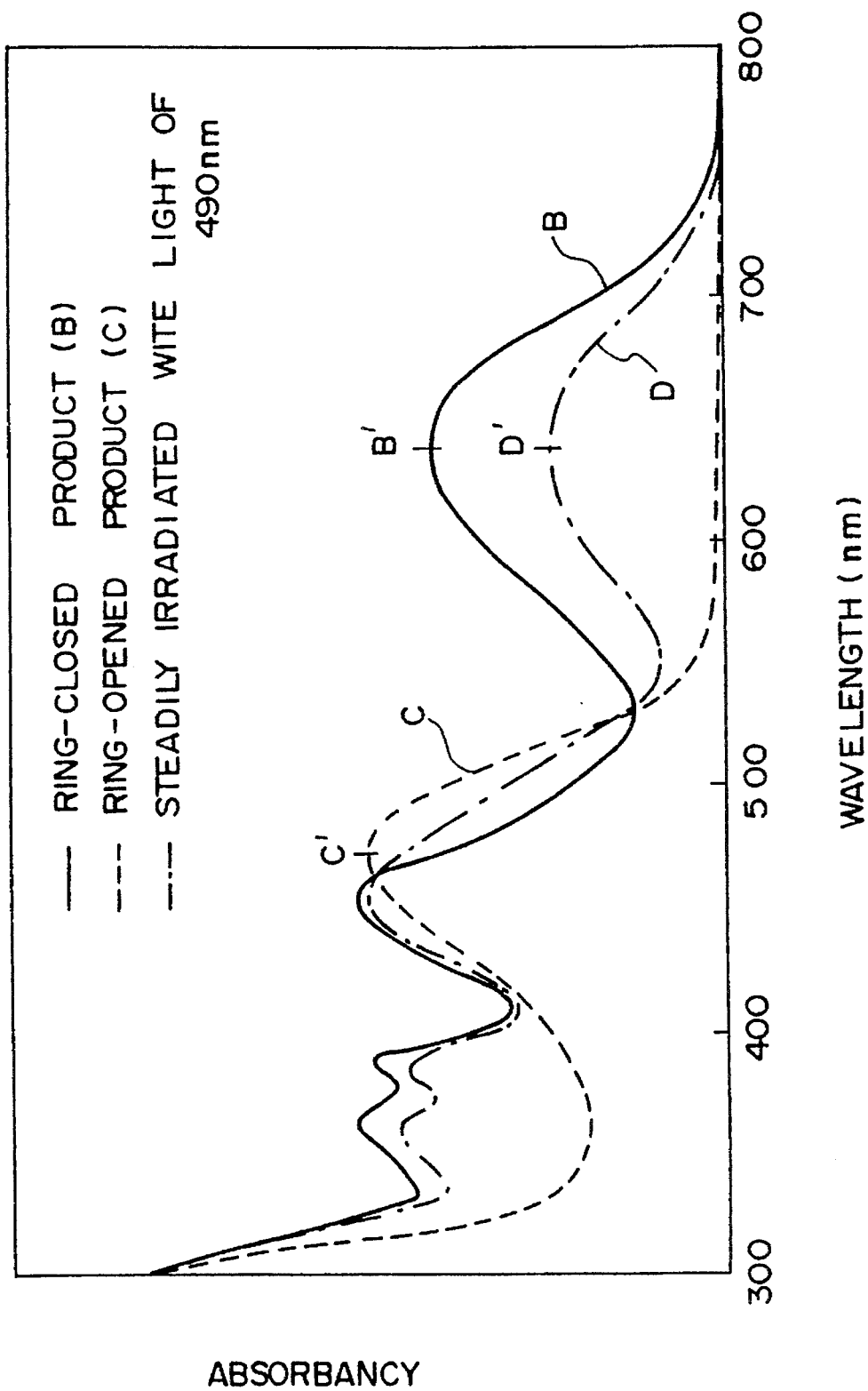
FIG. 5 is a diagram of an absorption spectrum of the compound 4 of the Example.

The solution of the ring-closed product was dried under reduced pressure, dissolved in hexane, and the absorption spectrum of the ring-closed product only was measured (curve B in FIG. 5).

The solution of the ring-closed product was irradiated with the light of 550 nm or longer obtained through a cut filter to render it to be the ring-opened product in order to measure its absorption spectrum (curve C in FIG. 5).

Then, the solution of the ring-opened product was steadily irradiated with a ray of active light of 490 nm, in order to measure the absorption spectrum (curve D in FIG. 5) The absorption spectra of the solutions were measured by using a spectrophonometer, Model UV-3400A manufactured by Hitachi, Ltd.

[Example 3]

The compounds 1, 2, 3, 4 and 6 were dissolved in benzene (spectrum grade, produced by Kishida Kagaku Co.) and in hexane (spectrum grade, produced by Kishida Kagaku Co.), and were steadily irradiated with a ray of active light of 490 nm. The isomerization factors of the compounds into the ring-closed products thereof and maximum absorption wavelengths (λmax nm) in the absorption spectra were as follows:

| Compound 4: | λmax 639 nm |
| | 65% in hexane |
| | 10% in benzene |
| Compound 3: | 55% in hexane |
| | 16.7% in benzene |
| Compound 6: | λmax 640 nm |
| | 50% or less in hexane |
| Compound 2: | λmax 607 nm |
| | 50% in hexane |
| | 10% in benzene |
| Compound 1: | 55% in hexane |
| | 17.7% in benzene |

The isomerization factors were calculated as described below. Referring, for example, to the compound 4, the absorbancy of FIG. 5 was used, and the isomerization factor in hexane was calculated in accordance with D/B'×100 to be 65.

[Example 4]

The compounds 1 and 3 were dissolved in the mixture solutions of hexane (spectrum grade, produced by Kishida Co.) and benzene (spectrum grade, produced by Kishida Co.) of the ratios of 80:20, 60:40, 40:60, 20:80 and 0:100, and were steadily irradiated with a ray of active light of 490 nm. The isomerization factors of the compounds from the ring-opened products thereof into the ring-opened products thereof were as shown in FIG. 1, with the value in hexane being set to 1.

[Example 5]

Relative quantum yields $\phi$, $\phi'$ and extinction coefficients $\epsilon$, $\epsilon'$ of the ring-closed products and the ring-opened products of the compounds 2 and 4 were found according to methods described below. The results were as shown in Table 1.

Measuring Method

Using a fulgide [ring-opening reaction: $\phi_1 = 0.048$ (492 nm), $\epsilon_1 = 8200$] of which the quantum yield has been known having the following formula,

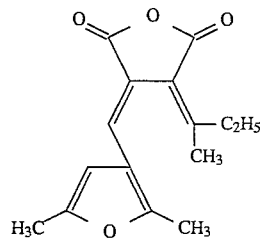

the quantity of light I at 492 nm was found by using an actinometer (research radiometer, IN1700, manufactured by international Light Co.). The result was set to be $\alpha$, and $I_1 = 492\alpha$.

Then, a hexane solution of the fulgide having a sufficiently low absorbancy (which is optically thin) was prepared (absorbancy at a wavelength of 492 nm of 0.2 abs).

The above solution was irradiated with the light of 492 nm to effect the ring-opening reaction, and log A was plotted with respect to the irradiation time t, where A denotes the absorbancy λmax (492 nm) of the ring-closed product after irradiated for the time t. Then, a gradient $\Delta_1$ of the obtained line was found.

Then, a hexane solution of the compound 4 having a sufficiently low absorbancy was prepared (absorbancy at a wavelength of 490 nm of 0.2 abs), irradiated with the light of 490 nm, and log A was plotted with respect to the irradiation time t in order to find a gradient $\Delta_2$ of the obtained line in the same manner as described above, where A denotes the absorbancy λmax (639 nm) of the ring-closed product after irradiated for the time t.

Furthermore, the quantity of light at an excitation wavelength 490 nm in the ring-closing reaction of the compound 4 was measured by using the actinometer. The quantity of light was set to be $\beta$, and $I_2 = 490\beta$.

From the above results, the following formula holds, $$\Delta 1 : \Delta 2 = \epsilon 1 \times \phi 1 \times I1 : \epsilon \times \phi \times I2$$
$$= 8200 \times 0.048 \times 492\alpha : 6200 \times \phi \times 490\beta$$

From the above formula, therefore, the relative quantum yield $\phi$ of the ring-closed product of the compound 4 was found. It is possible to find the quantum yield $\phi$ of the ring-closed product of the compound 2 in the same manner as described above.

Moreover, a hexane solution of the compound 4 having a sufficiently low absorbancy was prepared (absorbancy at a wavelength of 639 nm of 0.2 abs), irradiated with the light of 639 nm, and log A was plotted with respect to the irradiation time t in order to find a gradient $\Delta_3$ of the obtained line in the same manner as described above, where A denotes the absorbancy λmax (639 nm) of the ring-closed product after irradiated for the time t.

Furthermore, the quantity of light at an excitation wavelength 639 nm in the ring-opening reaction of the compound 4 was measured by using the actinometer. The quantity of light was set to be γ, and $I_2'=639\gamma$.

From the above results, the following formula holds, $$\Delta 1 : \Delta 3 = \epsilon 1 \times \phi 1 \times I1 : \epsilon' \times \phi' \times I2'$$
$$= 8200 \times 0.048 \times 492\alpha : 6200 \times \phi' \times 639\alpha$$

From the above formula, therefore, the relative quantum yield $\phi'$ of the ring-opened product of the compound 4 was found. It is possible to find the quantum yield of the ring-opened product of the compound 2 in the same manner as described above.

TABLE 1

| Compound | $\phi$ Ring-closing reaction | $\phi'$ Ring-opening reaction | $\epsilon$ Ring-closed product | $\epsilon'$ Ring-opened product |
| --- | --- | --- | --- | --- |
| 2 | 1 | 1 | 10000 | 8200 |
| 4 | 2.1 | 1.1 | 6200 | 7500 |
| 7 | 1.8 | 0.3 | 10000 | 8300 |

[Example 6]

The laminated plate of Example 1 was sufficiently irradiated with the light of 490 to 500 nm to prepare a recording plate of a vivid green color which was then exposed to an image-bearing light of an argon-ion laser beam. There was obtained a material recording an image of a dense yellow color maintaining vividness and high contrast.

[Example 7]

A laminated plate was obtained in the same manner as in Example 1 but using the compound 7 and was sufficiently irradiated with the light of 500 nm to prepare a recording plate of a green color. The recording plate was exposed to an image-bearing light of 663 nm. There was obtained a material recording an image of a dense red color maintaining vividness and high contrast.

We claim:

1. A compound represented by the following formula:

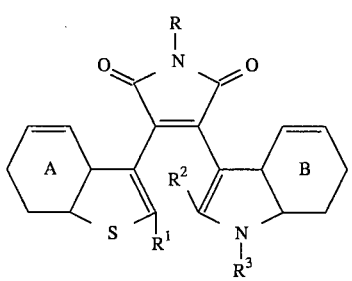

or the following formula (2):

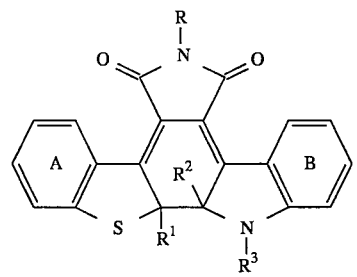

wherein R is a monovalent hydrocarbon group selected from the group consisting of lower alkyl, phenyl, tolyl, benzyl and phenethyl, or said monovalent hydrocarbon group substituted with a cyano group, an amide group, a carboxyl group or an alkoxycarbonyl group;

$R^1$ and $R^2$, independently, represent a member selected from the group consisting of a hydrogen atom, a lower alkyl group and a group of the formula —$XR^4$, where X represents an oxygen atom or a sulfur atom and $R^4$ represents a lower alkyl group, with the proviso that at least one of $R^1$ and $R^2$ is an alkoxy group or alkylthio group represented by the formula —$XR^4$;

$R^3$ is an alkyl group of from about 8 to about 26 carbon atoms or an acyl group of from 2 to about 26 carbon atoms; and benzene rings A and B may each have a substituent selected from the group consisting of a lower alkyl group, a lower alkoxy group and a halogen atom.

2. A compound according to claim 1, having the formula (1) wherein $R^1$ is the group of formula —$XR^4$, where X represents a sulfur atom and $R^2$ is an alkyl group.

3. A compound according to claim 1, having the formula (1) wherein $R^1$ is the group of formula —$XR^4$, where X represents an oxygen atom, and $R^2$ is an alkyl group.

4. A compound according to claim 1, having the formula (1) wherein R is a cyanoalkyl group.

5. A compound according to claim 1, having the formula (2) wherein $R^1$ is the group of formula —$XR^4$, where X represents a sulfur atom and $R^2$ is an alkyl group.

6. A compound according to claim 1, having the formula (2) wherein $R^1$ is the group of formula —$XR^4$, where X represents an oxygen atom, and $R^2$ is an alkyl group.

7. A compound according to claim 1, having the formula (2) wherein R is a cyanoalkyl group.

8. A compound according to claim 1 wherein

R represents lower alkyl or lower alkyl substituted with a cyano group, an amide group, a carboxyl group or an alkoxy carbonyl group;

$R^1$ and $R^2$, are as defined; and $R^3$ represents an alkyl group of from about 12 to about 22 carbon atoms or an acyl group of from 2 to about 18 carbon atoms.

9. A compound according to claim 1 wherein

R represents cyanomethyl;

$R^1$ and $R^2$ are as defined; and $R^3$ represent alkyl or acyl group of from about 12 to about 22 carbon atoms.

* * * * *